United States Patent
Langan et al.

(10) Patent No.: US 10,732,798 B2
(45) Date of Patent: Aug. 4, 2020

(54) INTERFACE DISPLAY FOR INFUSION MODULE

(71) Applicant: CAREFUSION 303, INC., San Diego, CA (US)

(72) Inventors: John Langan, San Diego, CA (US);
Tressa Daniels, San Diego, CA (US);
Craig Mitchell, San Diego, CA (US);
Wendy Smyth, San Diego, CA (US);
Kelly Daoust, San Diego, CA (US);
Laura Collins, San Diego, CA (US);
Patricia West, San Diego, CA (US);
Claire Knight, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 36 days.

(21) Appl. No.: 15/984,277

(22) Filed: May 18, 2018

(65) Prior Publication Data

US 2019/0354243 A1  Nov. 21, 2019

(51) Int. Cl.
*G06F 3/0482* (2013.01)
*A61M 5/14* (2006.01)
*G06F 3/147* (2006.01)

(52) U.S. Cl.
CPC ......... *G06F 3/0482* (2013.01); *A61M 5/1413* (2013.01); *G06F 3/147* (2013.01);
(Continued)

(58) Field of Classification Search
CPC ............................ G06F 3/0482; A61M 5/1413
See application file for complete search history.

(56) References Cited

U.S. PATENT DOCUMENTS

2005/0137653 A1* 6/2005 Friedman ............. A61B 5/0002
607/60
2010/0095240 A1* 4/2010 Shiplacoff ............. G06F 3/0483
715/784
(Continued)

FOREIGN PATENT DOCUMENTS

WO     WO-0145774 A1     6/2001
WO     WO-2015031802 A1  3/2015

OTHER PUBLICATIONS

International Search Report and Written Opinion for Application No. PCT/US2019/032870, dated Aug. 9, 2019, 15 pages.

*Primary Examiner* — Seth A Silverman
(74) *Attorney, Agent, or Firm* — Morgan, Lewis & Bockius LLP

(57) ABSTRACT

A method including receiving, in a main frame of a patient care unit, an infusion information from a medication delivery module coupled with the main frame is provided. The medication delivery module being mounted on a plug-in port associated with the main frame. The method also includes displaying, on a display in the main frame, an individual channel card including at least a portion of the infusion information from the medication delivery module and orienting an edge of the individual channel card toward a location of the plug-in port relative to the main frame, the edge having a visual indicator that visually indicates an orientation of the module associated with the individual channel card. The method also includes expanding the individual channel card to display a detailed portion of the infusion information upon receipt of a user selection. A system and a non-transitory, computer readable medium including instructions to perform the above method are also provided.

20 Claims, 9 Drawing Sheets

(52) U.S. Cl.
CPC . *A61M 2205/14* (2013.01); *A61M 2205/3334* (2013.01); *A61M 2205/3368* (2013.01); *A61M 2205/3592* (2013.01); *A61M 2205/50* (2013.01); *A61M 2205/502* (2013.01); *A61M 2205/505* (2013.01); *A61M 2205/584* (2013.01); *A61M 2209/086* (2013.01)

(56) References Cited

U.S. PATENT DOCUMENTS

| | | | |
|---|---|---|---|
| 2011/0083111 A1* | 4/2011 | Forutanpour | H04W 4/21 |
| | | | 715/863 |
| 2013/0317753 A1 | 11/2013 | Kamen et al. | |
| 2014/0362294 A1* | 12/2014 | Majid | H04N 5/445 |
| | | | 348/564 |
| 2016/0095976 A1 | 4/2016 | Simpson et al. | |
| 2018/0214634 A1* | 8/2018 | Neftel | A61M 5/16854 |

* cited by examiner

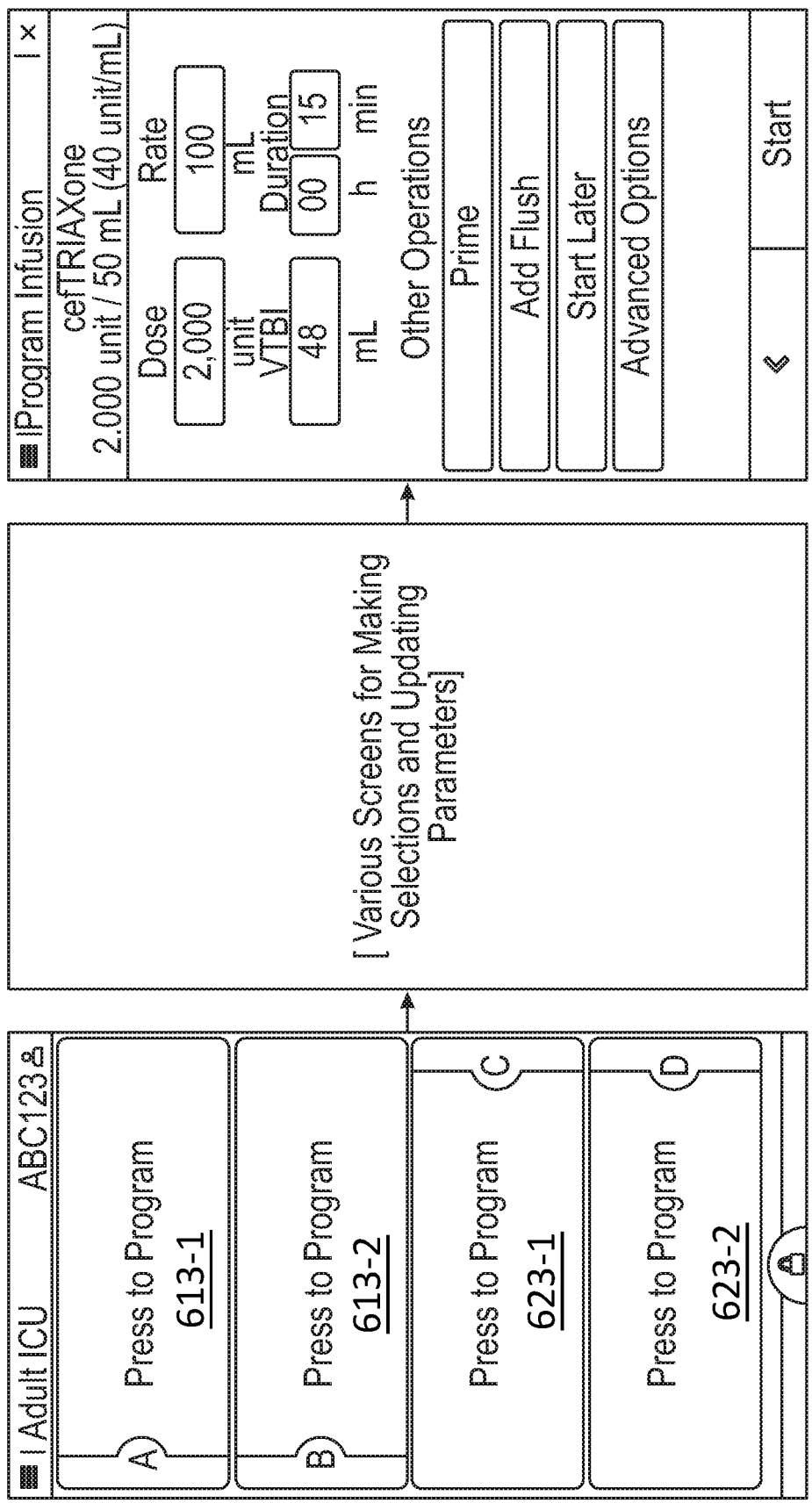

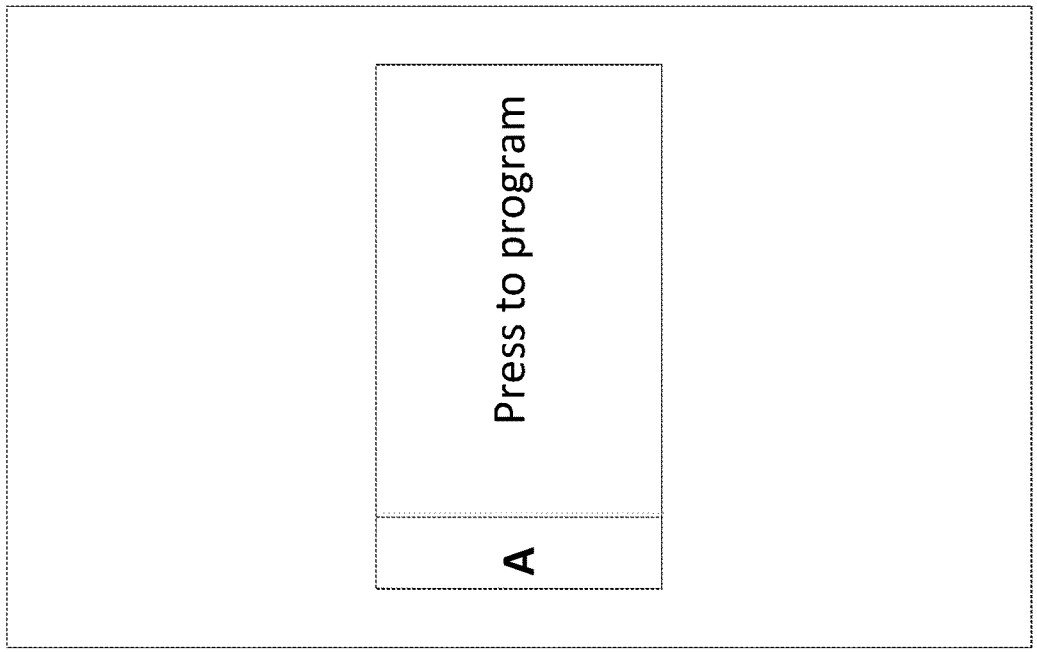

US 10,732,798 B2

INTERFACE DISPLAY FOR INFUSION MODULE

TECHNICAL FIELD

The present disclosure is generally related to a patient care unit (PCU) configured for medication delivery. More specifically, the present disclosure relates to methods and systems to display infusion information in expandable patient care units having multiple medication delivery modules.

BACKGROUND

Patient care units such as infusion medication devices may include modular platforms that are expandable with multiple medication delivery modules to handle more than one type of medication delivery to a patient. As the infusion module is expanded, typically each individual infusion type device in the module provides its own user display and interface. This may result in a wide variety of display types that may confuse or distract the user during infusion and other medication delivery procedures. Further, alert notifications when one or more of the medication delivery modules in the patient care unit is not performing appropriately may be lost or hard to notice for a user.

SUMMARY

In a first embodiment, a computer-implemented method includes receiving, in a main frame of a patient care unit, infusion information from a first medication delivery module electronically coupled to the main frame via a first plug-in port associated with the main frame; displaying, on a display of the main frame, a first graphical channel card comprising at least a portion of the infusion information received from the first medication delivery module, the first graphical channel card having a first visual indicator along an edge of the first graphical channel card; dynamically orienting the edge of the first graphical channel card and the first visual indicator toward a location, relative to the main frame, of the first plug-in port and the first medication delivery module; receiving a user selection at the main frame; and expanding the first graphical channel card to display a detailed portion of the infusion information upon receipt of a user selection. Other aspects include corresponding systems, apparatus, and computer program products for implementation of the method.

In some embodiments a system includes a memory storing instructions and one or more processors coupled with the memory and configured to execute the instructions to cause the system to receive, in a main frame of a patient care unit, a first infusion information from a first medication delivery module electronically coupled with the main frame via a first plug-in port associated with the main frame; display, in the main frame, a first graphical channel card comprising at least a portion of the first infusion information from the first medication delivery module, the first graphical channel card having a first visual indicator along an edge of the first graphical channel card; dynamically orient the first graphical channel card toward a location of the first plug-in port relative to the main frame; determine that a second medication delivery module was electronically coupled to the main frame via a second plug-in port associated with the main frame on a side of the main frame opposite to the first plug-in port; receive a second infusion information from the second medication delivery module; and dynamically display the second infusion information in a second graphical channel card on the display of the main frame, adjacent to the first graphical channel card, with a visual indicator of the second graphical channel card oriented toward the second medication delivery module. Other aspects include corresponding methods, apparatus, and computer program products for implementation of the system.

In further embodiments, a non-transitory, computer-readable medium stores instructions which, when executed by a processor in a computer, cause the computer to perform a method. The method includes receiving, in a main frame of a patient care unit, an infusion information from a first medication delivery module electronically coupled with the main frame via a first plug-in port associated with the main frame; displaying, on a display of the main frame, a first graphical channel card comprising at least a portion of the infusion information received from the first medication delivery module, the first graphical channel card having a first visual indicator along an edge of the first graphical channel card; orienting the first graphical channel card toward a location of the first plug-in port relative to the main frame so that the edge and the first visual indicator are oriented towards a side of the main frame corresponding to the first plug-in port; and expanding the first graphical channel card, from a first summary state to a second detail state, to display a detailed portion of the infusion information upon receipt of a user selection. Other aspects include corresponding systems, apparatus, methods, and computer program products for implementation of the computer-readable medium.

BRIEF DESCRIPTION OF THE DRAWINGS

FIGS. 6A-6G illustrates example channel cards that may be expanded and contracted according to various implementations.

In the figures, elements having the same or similar reference numeral have the same or similar functionality or configuration, unless expressly stated otherwise.

DETAILED DESCRIPTION

Embodiments as disclosed herein include PCUs that are configured to be expanded with multiple medication delivery modules to handle delivery of more than one type of medication to a patient. The PCU includes a main frame having a main display that displays medication delivery information received from each of the individual medication delivery modules. Accordingly, embodiments as disclosed herein provide a uniform display type for the different medication delivery units, to avoid user confusion or distraction. Also, by providing a uniform data display across multiple types of medication delivery modules, embodiments as disclosed herein facilitate a user verification and validation, reducing the time a user needs to confirm or adjust any of the medication delivery settings (e.g., in case of an emergency). In some embodiments an alert notification may be displayed prominently in a main frame of the PCU, when one or more of the medication delivery modules is not performing appropriately.

Some of the advantages of embodiments consistent with the present disclosure include an improved safety in medication delivery protocols. Embodiments as disclosed herein are suitable for emergency situations when a rapid action is desirable, e.g., when a medication delivery module stops working, or continues to deliver medication when it should stop, provides the wrong medication, the wrong dose, or at the wrong rate. Some of the emergency situations may include determining that a certain fluid or medication container will be emptied before the total dose is delivered to the patient. Accordingly, a quick action by a nurse or other personnel may resolve the emergency before it becomes a more serious problem.

Figure 1:
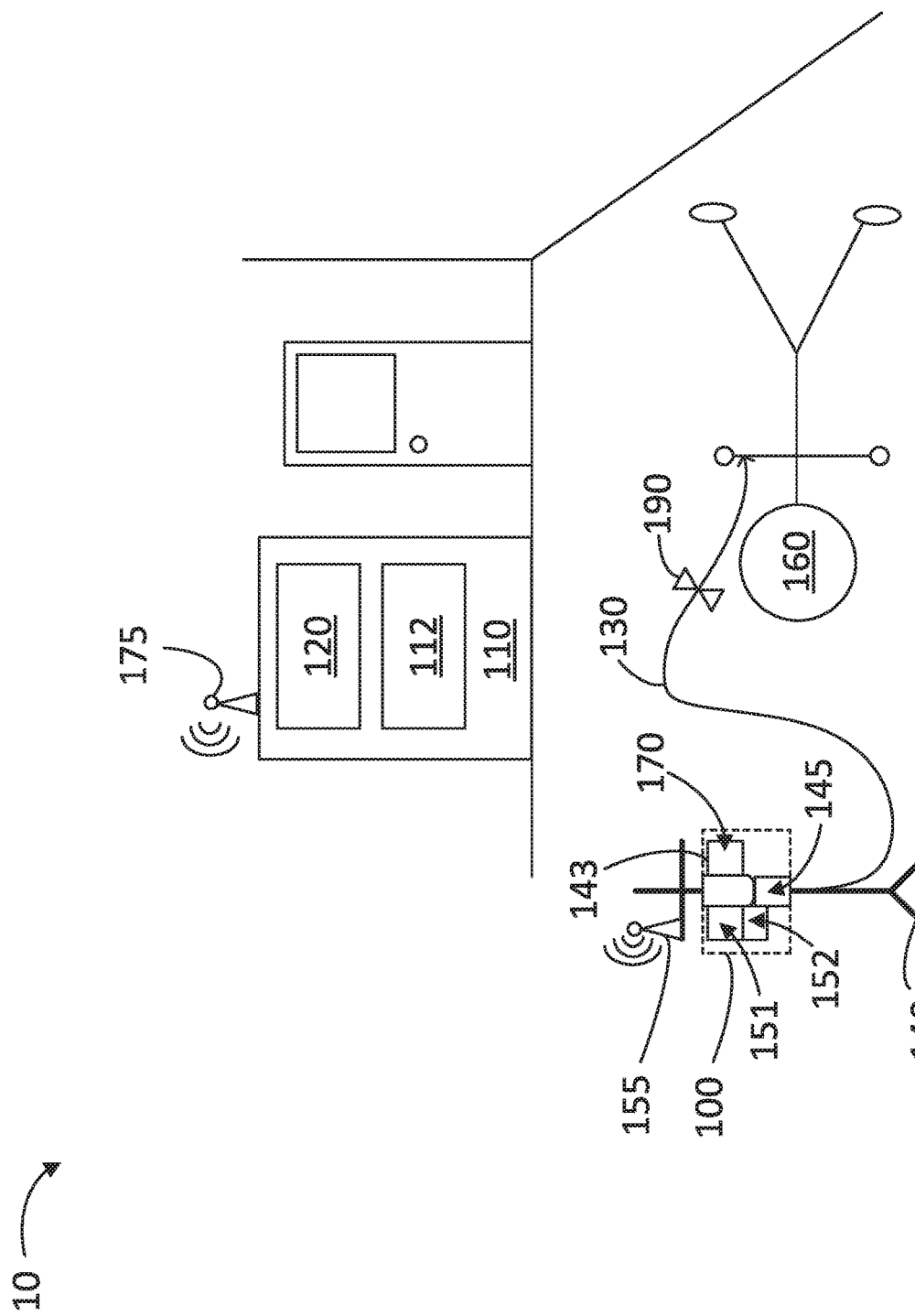
FIG. 1 illustrates a medication delivery system including a patient care unit and a controller, according to some embodiments.

FIG. 1 illustrates a medication delivery system 10 including a patient care unit (PCU) 100 and a controller 110, according to some embodiments. Medication delivery system 10 may include a frame 140 supporting a container 143 having a fluid 170.

In some embodiments, medication delivery system 10 is an intravenous delivery system and fluid 170 may include an intravenous fluid to be administered to patient 160 through a blood vessel. Accordingly, fluid 170 may include blood, plasma, or a medication. Fluid 170 may be any liquid suitable for intravenous delivery. Common intravenous liquids include crystalloids (e.g., saline, Lactated Ringers, glucose, dextrose), colloids (e.g., hydroxyethyl starch, gelatin), liquid medications, buffer solutions, and blood products (e.g., packed red blood cells, plasma, clotting factors) or blood substitutes (e.g., artificial blood) that are desired to be injected intravenously to a patient 160. A fluid line 130 carries fluid 170 from container 143 to patient 160. In some embodiments, PCU 100 includes a pump 145 to move fluid 170 through fluid line 130.

Medication delivery system 10 includes a PCU 100 mechanically coupled with fluid line 130. In some embodiments, PCU 100 is configured to provide multiple measurements of the fluid flow. In some embodiments, PCU 100 is configured to measure fluid pressure, fluid flow rate, and the like. PCU 100 may include a memory 151 storing instructions which, when executed by a processor 152, cause PCU 100 to perform, at least partially, steps in methods as disclosed herein.

In some embodiments, the operation of PCU 100 may be controlled wirelessly by a remote controller 110 located, for example, at a nurse station. The wireless communication may be performed by an antenna 175 on the controller side and an antenna 155 on frame 140. Controller 110 includes a processor 112 and a memory 120. Memory 120 may include commands and instructions, which when executed by processor 112, cause controller 110 to perform at least partially some of the steps included in methods consistent with the present disclosure. Furthermore, PCU 100 may wirelessly communicate with controller 110 via antenna 155, to receive instructions from and provide data to, controller 110. In some embodiments, PCU 100 is configured to provide a visual status (e.g., a progress report) of the medication delivery (e.g., for a nurse or other medication personnel), and to transmit the visual status and other medication delivery information to controller 110.

Memory 120 in controller 110 stores clinical information related to the medication delivery. Accordingly, controller 110 provides PCU 100 at least the dynamic part of the clinical information, including the total amount of medication to be delivered, at what rate, at what time to start delivery, and at what time to stop, or pause, the medication delivery. PCU 100 provides, to controller 110, a status of how far it has progressed to a certain delivery goal. Further, in some embodiments PCU 100 stores at least a portion of the clinical information, and a status of the medication delivery in memory 151.

In some embodiments, a second controller 110 may take over control of PCU 100 (e.g., when a patient is transferred from one room or unit to another and a first controller stays in the room while a second controller moves with the patient).

Controller 110, and PCU 100 may communicate through antennas 155 and 175 via a Bluetooth, Wi-Fi, or any other radio-frequency protocol. Accordingly, controller 110 may be configured to process data from PCU 100 and store a medication delivery progress update in memory 120. In some embodiments, other characteristics of the fluid relevant for a medication delivery or infusion may be stored by controller 110 in memory 120. A valve 190 in fluid line 130 may be operated to allow fluid 170 to flow into patient 160 when PCU 100 detects a bubble content lower than a predetermined threshold. In some embodiments, valve 190 may be closed by a motor in PCU 100 (e.g., an occlusion is detected in fluid line 130, or a bubble level is above a pre-selected threshold).

Furthermore, controller 110 may provide an alarm to a centralized system when a bubble count in PCU 100 becomes higher than a threshold. In some embodiments, controller 110 may also provide commands to regulate the temperature of fluid 170 (e.g., via a thermostat) based on a bubble count or a temperature measurement provided by PCU 100.

Figure 2:
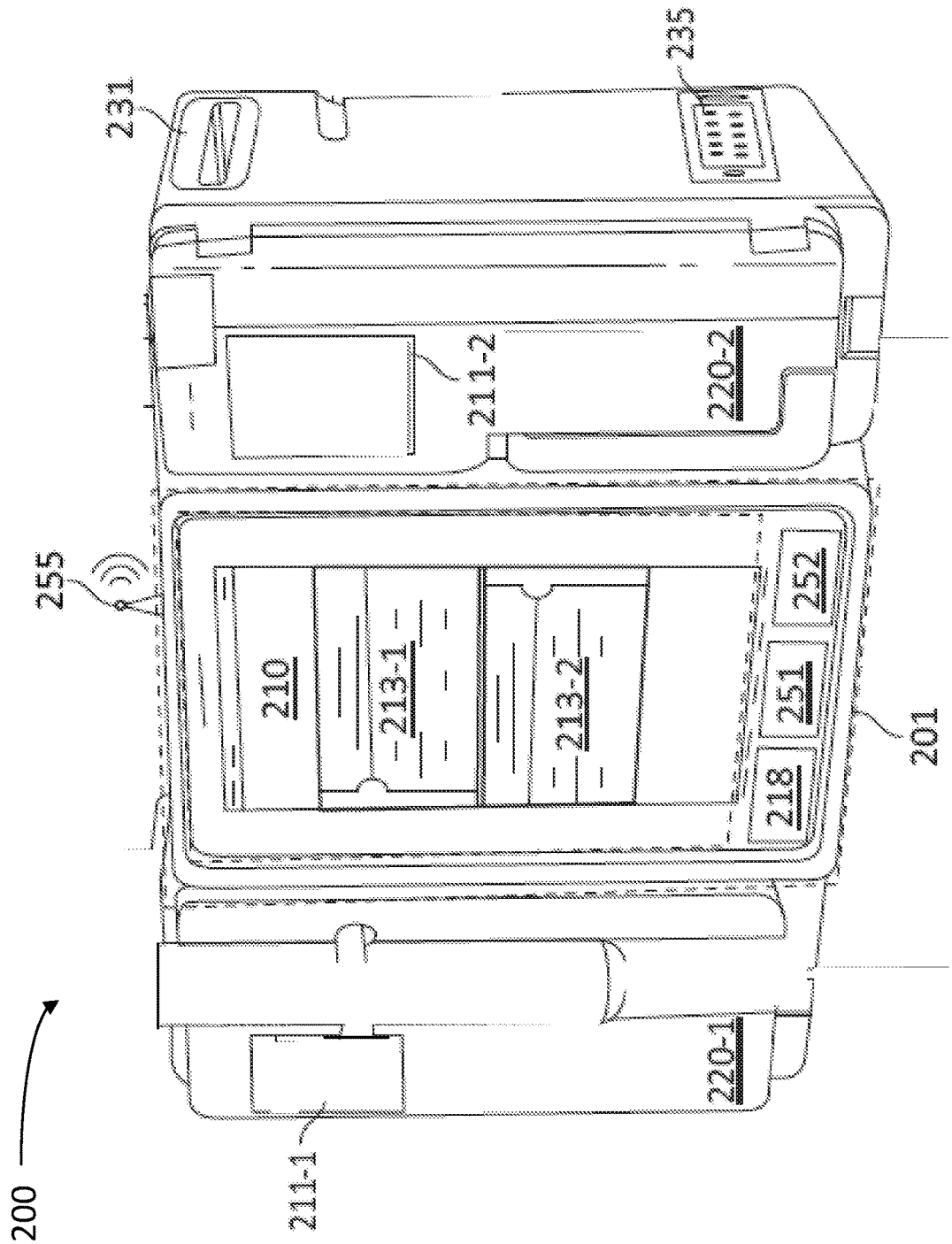
FIG. 2 illustrates a patient care unit expanded with medication delivery modules, according to some embodiments.

FIG. 2 illustrates a PCU 200 including a main frame 201 expanded with medication delivery modules 220-1 and 220-2 (hereinafter, collectively referred to as "medication delivery modules 220"), according to some embodiments. In some embodiments, medication delivery modules 220 include plug-in ports 231 and 235 for expansion. Accordingly, a new medication delivery module may be attached to PCU 200 by coupling a connector through plug-in ports 231 and 235. Plug-in port 235 may include electrical terminals so that the added medication delivery module 220 may transmit and receive information to and from a main frame 201. In some embodiments, the added medication delivery module 220 may also receive power from main frame 201 through the plug-in port 235. Main frame 201 may include a main display 210, a memory 251 and a processor 252 (e.g., memory 151 and processor 152). Module displays 211-1 and 211-2 (hereinafter, collectively referred to as "module displays 211") may be configured to display medication delivery status and further information associated with each of medication delivery modules 220.

Main display 210 is configured to display individual channel cards 213-1 and 213-2 (hereinafter, collectively referred to as "graphic channel cards" or "individual channel cards 213"). Each individual channel card 213 graphically displays information received from a respective one of medication modules 220, including information also displayed on a corresponding module displays 211. In some embodiments, main frame 201 includes a communications module 218 and an antenna 255, configured to communicate wirelessly with a controller (e.g., controller 110), or with a network.

Figure 3:
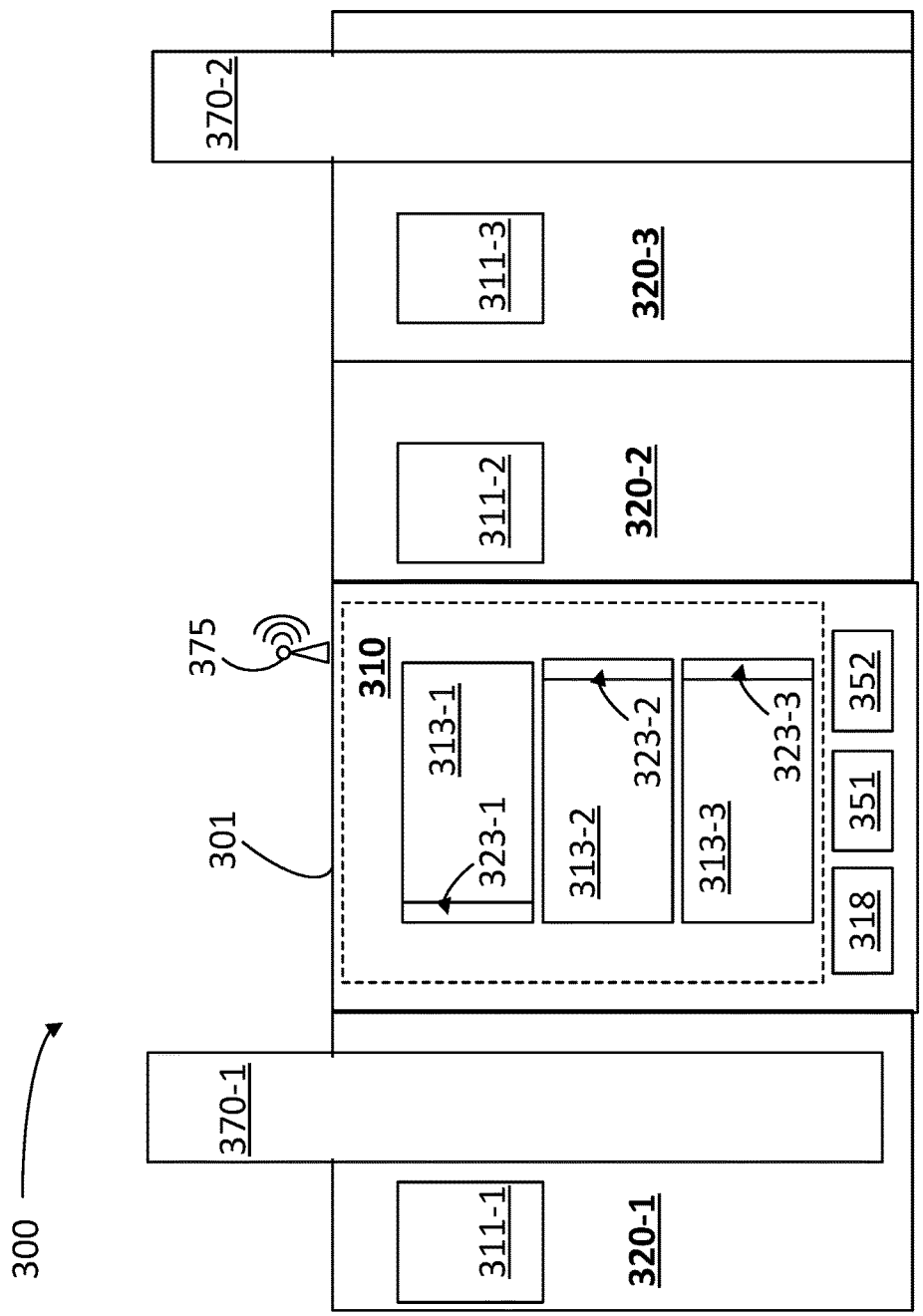
FIG. 3 illustrates a patient care unit including a main display mirroring individual module screens, according to some embodiments.

FIG. 3 illustrates a PCU 300 including a main frame 301 having a main display 310 that mirrors individual module displays, 311-1, 311-2 and 311-3 (hereinafter, collectively referred to as "module displays 311"), according to some embodiments. Main frame 301 includes a memory 351 storing instructions and a processor 352 configured to execute the instructions to cause main frame 301 to perform at least partially some of the steps in methods as disclosed herein. In some embodiments, main frame 301 also includes a communications module 318 and an antenna 355, configured to communicate wirelessly with a controller (e.g., controller 110), or with a network.

Main frame 301 is expanded with a medication delivery module 320-1 that is configured to deliver a fluid 370-1, a medication delivery module 320-2, and a medication delivery module 320-3 configured to deliver a fluid 370-2. Medication delivery modules 320-1, 320-2 and 320-3 will be collectively referred to, hereinafter, as "medication delivery modules 320." Module displays 311 may be configured to display medication delivery status and further information associated with each of medication delivery modules 320.

Similarly to main display 210 in PCU 200, main display 310 includes individual channel cards 313-1, 313-2, and 313-3 (hereinafter, collectively referred to as "individual channel cards 313"). Individual channel cards 313 include graphically displayed information from each of module displays 311. In some embodiments, individual channel cards 313 may include visual indicators 323-1, 323-2, and 323-3, respectively (hereinafter, collectively referred to as "visual indicators 323") which may specify the orientation of the channel card. In various implementations, visual indicators 323 are graphics along an edge of a channel card. By virtue of which edge of the channel card a visual indicator is displayed, the visual indicator visually associates to a user the location of the corresponding medication delivery module. For example, visual indicator 323-1 is placed on the left side of identification card 313-1, indicating that medication delivery module 320-1 is plugged-in to the left of main frame 301. Likewise, visual indicator 323-2 is placed on the right side of identification card 313-2, indicating that medication delivery module 320-2 is plugged-in to the right of main frame 301. And visual indicator 323-3 is placed on the right side of identification card 313-3, indicating that medication delivery module 320-3 is plugged-in to the right of main frame 301.

In some embodiments, visual indicators 323 may include a distinct color banner to indicate a status of each of medication delivery modules 320 associated with them. For example, visual indicator 323-1 may include a green banner, indicating that medication delivery module 320-1 is active and working properly. Visual indicator 323-2 includes an orange banner, indicating that medication delivery module 320-2 may be paused, inactive, or may have an error condition. Visual indicator 323-3 includes a green banner, indicating that medication delivery module 320-3 is active and working properly. Other color codes may be used, e.g., a red banner may indicate a medication delivery module that has an alarm flag. In some embodiments, respective visual indicator 323 of an identification card 313 may also be configured to display a graphic indicating the amount of fluid that is being infused by a module 320 associated with the identification card 313. For example, visual indicator 323 may include a graphic of a fluid drop 373, or an animation of a fluid dripping (e.g., within the banner, along the edge).

In some embodiments, one of medication delivery modules 320 may be removed from PCU 300 to be installed or plugged-in to a second PCU. Accordingly, in some embodiments the infusion information in the corresponding module display 311 may still be displayed while the medication delivery module 320 is unplugged.

A first medication delivery module may be electronically coupled to a main frame via a first plug-in port associated with the main frame. In this regard, the plug-in port may be a plug-in port directly on a first side of the main frame, so that the module plugs directly into the plug-in port when it is mounted to the main frame (e.g., to receive module 311-2 in FIG. 3). Or, the plug-in port may be a plug-in port on a side of another module such that the first medication delivery module is electronically coupled to the main frame via the other module (e.g., to receive module 311-3 in FIG. 3). As medication delivery modules are installed, new graphic channel cards are displayed on the display of the main frame, each orientated toward a newly-installed module. The main frame may receive an indication that a second medication delivery module was electronically coupled to the main frame via a second plug-in port associated with the main frame at a side of the main frame opposite the first plug-in port and the first medication delivery module. The main frame may then dynamically display, on the display screen of the main frame in response to receiving the indication, a second graphical channel card including at least a portion of a second infusion information. The second graphical channel card is displayed oriented toward the second plug-in port and the second medication delivery module and opposite to a side of the main frame where the first medication delivery module is electronically coupled via the first plug-in port. As depicted in FIG. 3, the graphical channel cards are displayed adjacent to each other as they are newly-displayed on display 310.

Figure 4:
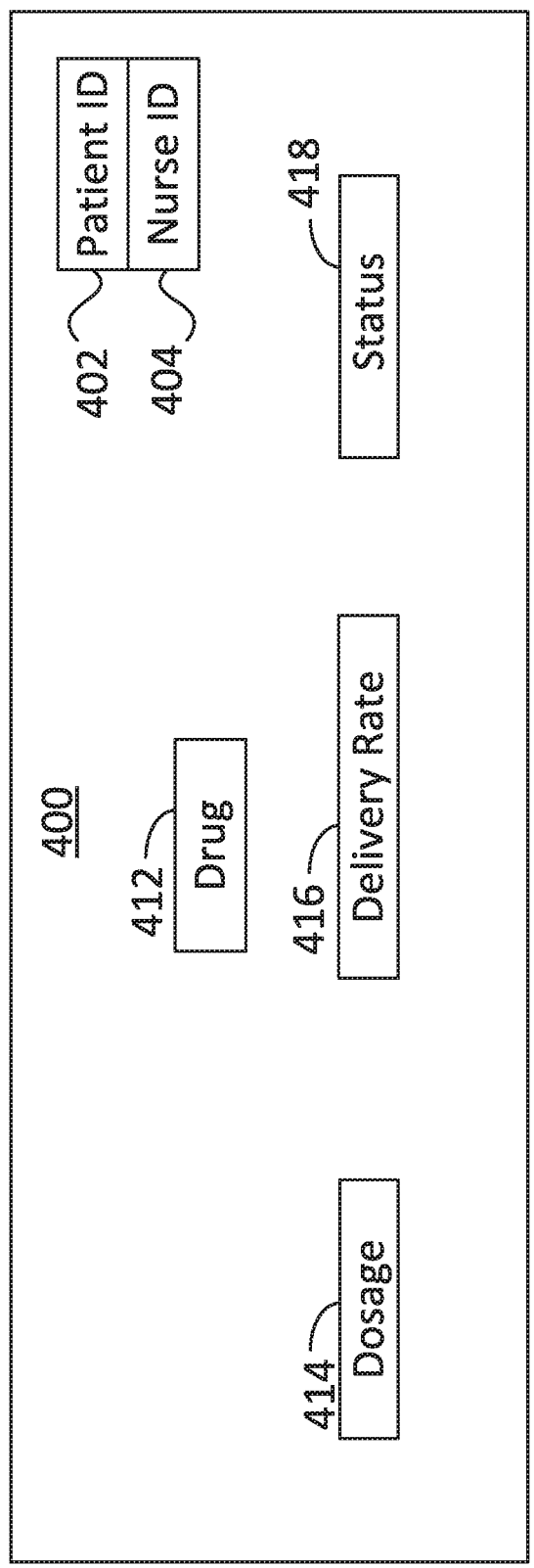
FIG. 4 illustrates a medication delivery data structure shared between a medication delivery module, a patient care unit, and a controller, according to some embodiments.

FIG. 4 illustrates a display of an infusion information 400 shared between a medication delivery module (e.g., medication delivery modules 220 and 320), a PCU (e.g., PCUs 100, 200 and 300), and a controller (e.g., controller 110), according to some embodiments. Infusion information 400 provides updated information about the settings of the medication delivery module, and a status of a medication delivery. According to various embodiments, infusion information 400 may be graphically displayed on a display screen, as shown in any of individual channel cards 213, or 313.

In some embodiments, infusion information 400 includes a patient identification (ID) 402, and a nurse ID 404. A medication name label ("Drug") 412 indicates the name of the drug configured for delivery to patient 402, under the care of nurse 404. According to various embodiments, infusion information 400 may include information pertaining to a fluid that is being infused by a module 320 (e.g., an amount, bolus, rate of infusion, etc.). When displayed, infusion information 400 may include a dosage indicator 414, a delivery rate indicator 416, and a status indicator 418. Status indicator 418 may indicate the amount of drug delivered to the patient.

Figure 5:
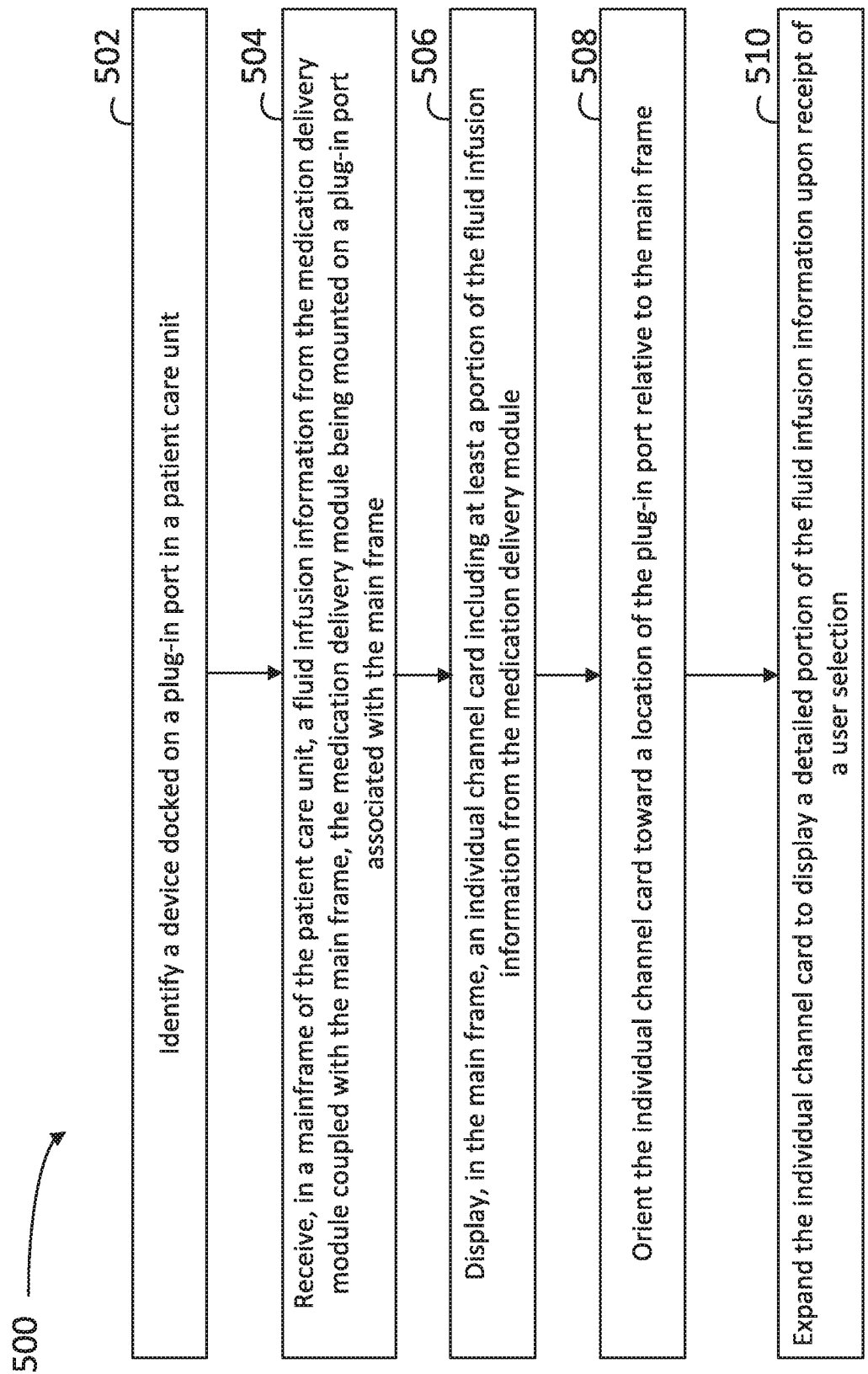
FIG. 5 illustrates a flowchart in a method for displaying a medication delivery information, according to some embodiments.

FIG. 5 illustrates a flowchart in a method 500 for displaying a medication delivery information, according to some embodiments. Method 500 may be performed at least partially by a PCU (e.g., PCUs 100, 200 and 300), while communicating with a controller (e.g., controller 110). At least some of the steps in method 500 may be performed by a computer having a processor executing commands stored in a memory of the computer (e.g., processors 112, 152, 252 and 352, and memories 120, 151, 251 and 351). In some embodiments, steps as disclosed in method 500 may include retrieving, editing, and/or storing files in a database that is part of, or is communicably coupled to, a memory (e.g., memories 251 and 351). In some embodiments, information transmitted between one or more devices in a system performing method 500 may include an infusion information (e.g., fluid infusion information 400). Methods consistent with the present disclosure may include at least some, but not all, of the steps illustrated in method 500, performed in a different sequence. Furthermore, methods consistent with the present disclosure may include at least two or more steps as in method 500 performed overlapping in time, or almost simultaneously.

Step 502 includes identifying a device docked on a plug-in port in a patient care unit. In some embodiments, step 502 includes verifying that the device is associated with a patient registered with a PCU associated with the module display.

Step 504 includes receiving, in the main frame of the patient care unit (e.g., main frames 201 or 301), an infusion information from the medication delivery module coupled with the main frame (e.g., medication delivery modules 220 or 320), the medication delivery module being mounted on a plug-in port associated with the main frame (e.g., plug-in ports 231 and 235). In some embodiments, the main frame comprises a memory circuit (e.g., memories 251 and 351), and step 504 includes storing the infusion information in the memory circuit.

Step 506 includes displaying, in the main frame, an individual channel card including at least a portion of the infusion information from the medication delivery module. In some embodiments, step 506 includes mirroring a display in the medication delivery module (e.g., displays 210 and 310). In some embodiments, step 506 includes providing a display information to a display in the medication delivery module. In some embodiments, step 506 includes displaying a fluid drop, or an animation of a dripping fluid when the medication delivery module is delivering an infusion. In some embodiments, step 506 includes displaying a second individual channel card including at least a portion of a second infusion information from a second medication delivery module coupled with the main frame. In some embodiments, step 506 includes providing a visual indicator in the individual channel card, the visual indicator comprising a color banner on a side of the individual channel card, the color banner consistent with a status of the medication delivery module, or an icon of a fluid drop (e.g., fluid drop 373), indicating active infusion.

Step 508 includes orienting the individual channel card toward a location of the plug-in port relative to the main frame. For example, in some embodiments, when there is a medication delivery module on either side of the main frame, two individual channel cards may be displayed in the main frame and step 508 may include orienting each of the two individual channel cards in opposite directions. Further, in some embodiments, step 508 may include changing the orientation of the individual channel card when the associated medication delivery module is switched from a plug-in port on one side of the main frame to a plug-in port on the other side of the main frame.

In yet some implementations, a step 508 may include a user moving the associated medication delivery module from one side of the main frame to the opposite side of the main frame, and obtaining the infusion information from the individual channel card associated with the medication delivery module and which has switched orientation to indicate the position change of the associated medication delivery module. In this regard, the main frame receives an indication that the first medication delivery module was electronically decoupled from a first plug-in port and then electronically coupled to the main frame via a second plug-in port associated with the main frame on a side of the main frame opposite the first plug-in port. The main frame then redisplays the channel card for the first medication delivery module and dynamically orients the edge of the channel card and the first visual indicator toward the second plug-in port.

Step 510 includes expanding the individual channel card to display a detailed portion of the infusion information upon receipt of a user selection. An individual channel card may be expanded or contracted dynamically (e.g., automatically) based on a number of active channels in the patient care unit, and/or a number of individual channel cards displayed on the same display screen. As described further with respect to FIG. 6A-6G, when expanded, an individual channel card may provide a more descriptive or detailed set of information regarding an infusion or parameters pertaining to the infusion.

In some embodiments, the module display comprises a touchscreen display, and step 510 includes receiving reprogramming commands for the device using the individual channel card in the touchscreen display. In some embodiments, the module display comprises a touchscreen display and step 510 includes detecting a touch by a user on the touchscreen display of the individual channel card. In some embodiments, step 510 includes issuing an alarm to a central server when the device docked on the plug-in port is not recognized by a PCU associated with the module display. In some embodiments, step 510 includes indicating, with the visual indicator, a state of the device docked on the plug-in port, wherein the state of the device comprises at least one of an error state and a running state. In some embodiments, step 510 includes adjusting a font size for the individual channel card to enhance a viewer perspective. In some embodiments, step 510 includes verifying that the medication delivery module is associated with a patient registered with the patient care unit. In some embodiments, the main frame comprises a communications module, and step 510 includes transmitting to a controller, via the communications module, the infusion information.

Figures 6D, 6E, 6F:
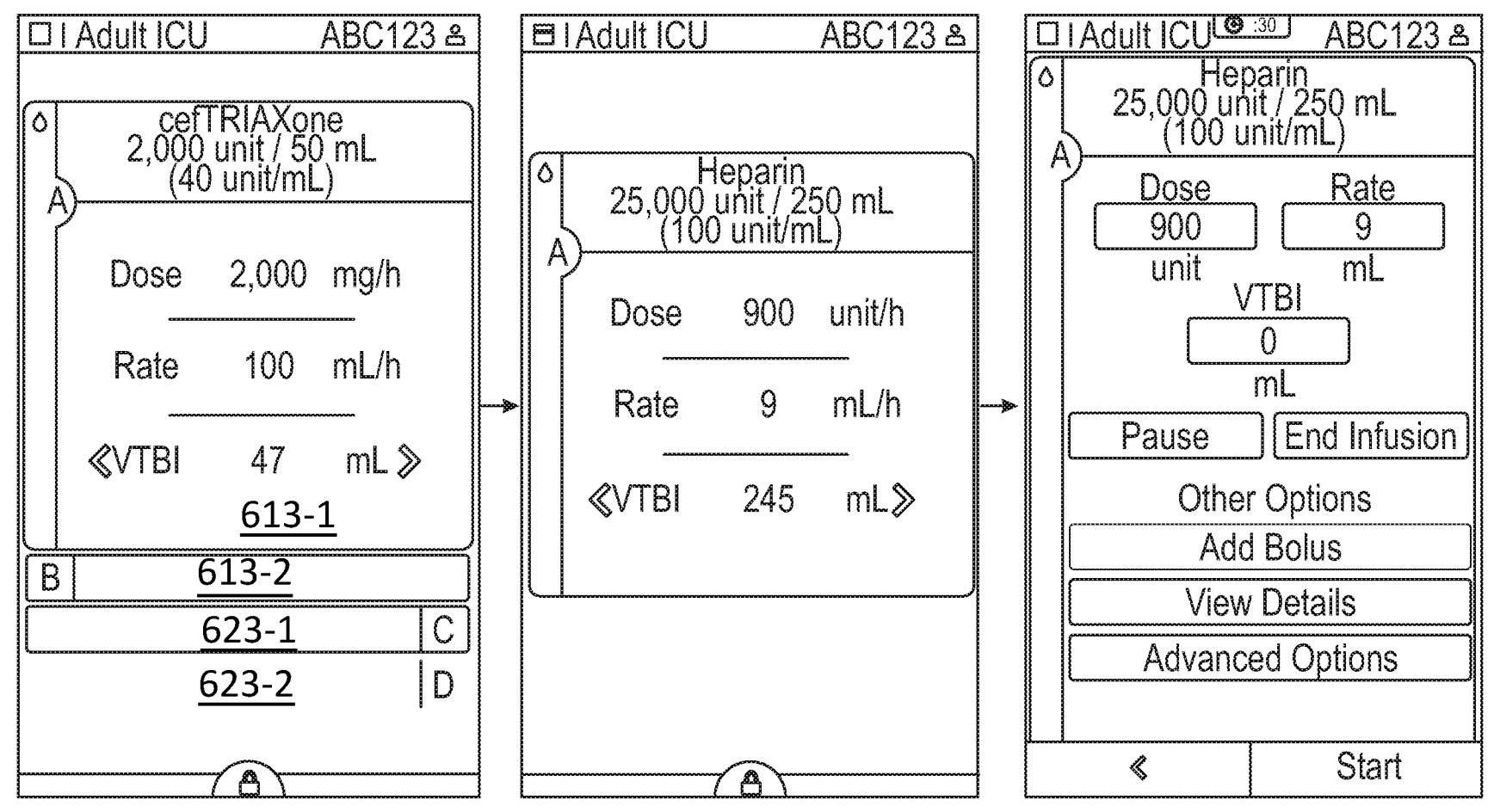

FIGS. 6A-6G are illustrations of example channel cards that may be expanded and contracted according to various implementations of the subject technology. FIG. 6A is an example of four channel cards being displayed on a main display (e.g., main display 310) for four respective individual channel cards (e.g., individual channel cards 313) corresponding to module displays (e.g., module displays 311). Channel cards A and B are aligned with their indicators to the left to represent medication delivery modules (e.g., medication delivery modules 320) attached to the left-hand side of main frame 301, and channel cards C and D are aligned with their indicators to the right to represent medication delivery modules attached to the right-hand side of the main frame (e.g., main frame 301).

Each channel card may be initially displayed without information. On selecting a channel card (e.g., channel card 613-1 A, 613-2 B, 623-1 C, or 623-2 D), the main display is updated to expand the channel card to an information screen (e.g., FIG. 6B) into which infusion parameters may be entered for storage in memory (e.g., in memory 120), for utilization in an infusion. FIG. 6C is an example of channel card A having been expanded to display descriptive or detailed set of information regarding an infusion or parameters pertaining to the infusion. Once the information has been entered, the card may be updated graphically, as shown by FIG. 6D, to display the information stored in memory, and parameters of an ongoing infusion. In the depicted example, FIG. 6D displays channel card A as displaying information for an actively programmed infusion operation programmed for a corresponding medication delivery module 320, while channel cards 613-2, 623-1 and 623-2 (B-D) are displayed without this information, indicating that the corresponding medication delivery modules have yet to be programmed.

FIG. 6E is an example of a channel card displaying information for an infusion operation of a corresponding medication delivery module. On selection of the channel card, the main display is updated as shown in FIG. 6F to display the channel card in an expanded state, with programming information displayed. The information displayed may include graphical or virtual buttons for activating and ending an infusion operation. FIG. 6G is an example of the channel card A returning to its preprogrammed state (e.g., no longer displaying infusion information 400) after the infusion operation is ended by virtual button input. In some aspects, a confirmation screen may be displayed requesting further confirmatory input from a user before a parameter is committed to an infusion operation or stored, or an active infusion operation is initiated or ended.

Figure 7:
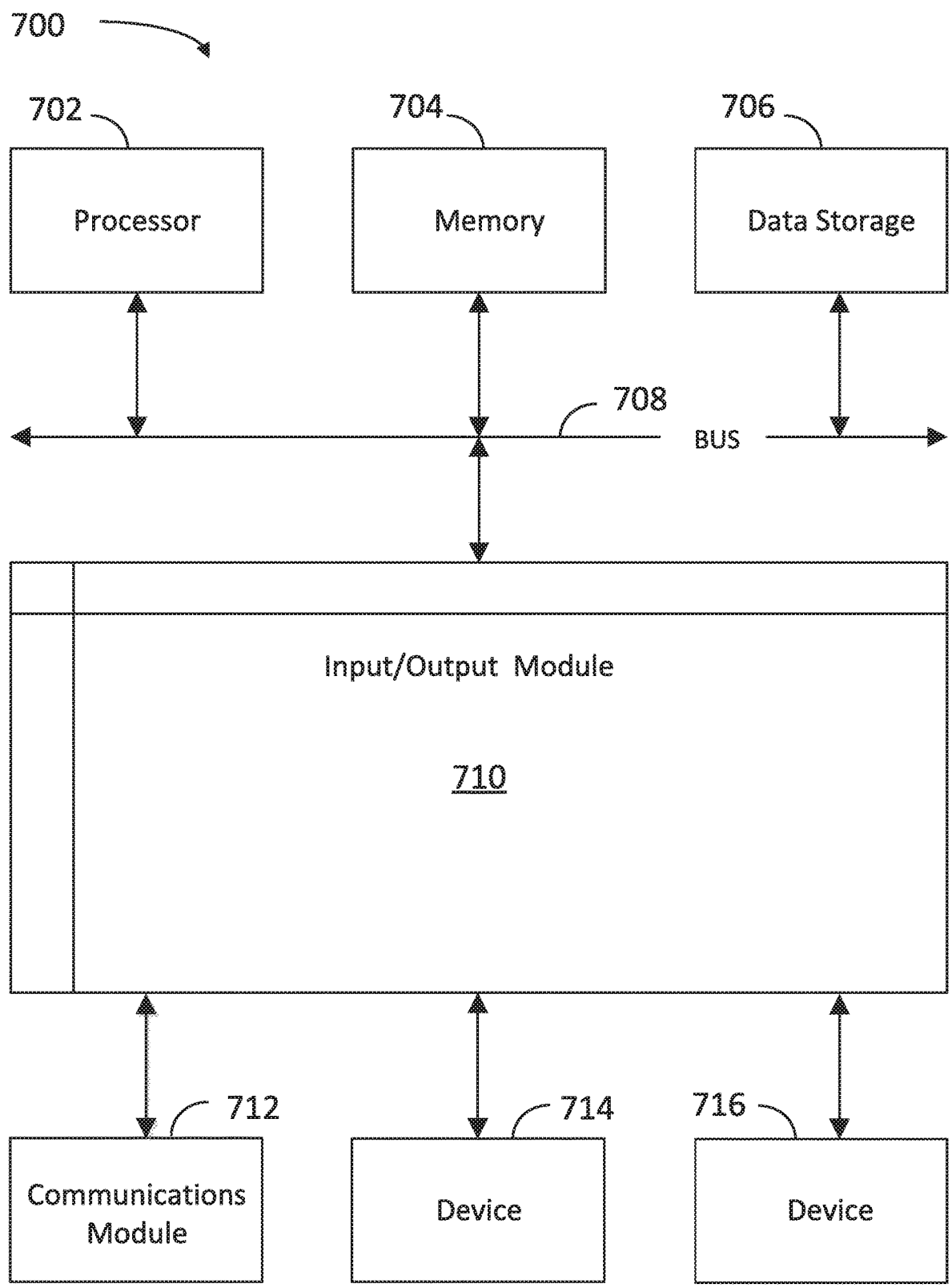
FIG. 7 is a block diagram illustrating an example computer system with which the client and server of FIGS. 1 and 2, and the method of FIG. 5 can be implemented, according to some embodiments.

FIG. 7 is a block diagram illustrating an example computer system 700 with which the client and server of FIGS. 1 and 2, and the method of FIG. 5 can be implemented, according to some embodiments. Computer system 700 (e.g., main frame 301) includes a bus 708 or other communication mechanism for communicating information, and a processor 702 (e.g., processors 152, 252 and 352) coupled with bus 708 for processing information. By way of example, the computer system 700 may be implemented with one or more processors 702. Processor 702 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 700 can include, in addition to hardware, a code that creates an execution environment for the computer program in question, e.g., code that constitutes processor firmware, a protocol stack, a database management system, an operating system, or a combination of one or more of them stored in an included memory 704 (e.g., memories 151, 251 and 351), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 708 for storing information and instructions to be executed by processor 702. The processor 702 and the memory 704 can be supplemented by, or incorporated in, a special purpose logic circuitry.

The instructions may be stored in the memory 704 and implemented in one or more computer program products, i.e., one or more modules of computer program instructions encoded on a computer readable medium for execution by, or to control the operation of, the computer system 700, and according to any method well known to those skilled in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, and xml-based languages. Memory 704 may also be used for storing temporary variable or other intermediate information during execution of instructions to be executed by processor 702.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 700 further includes a data storage device 706 such as a magnetic disk or optical disk, coupled to bus 708 for storing information and instructions. Computer system 700 may be coupled via input/output module 710 to various devices. Input/output module 610 can be any input/output module. Exemplary input/output modules 710 include data ports such as USB ports. The input/output module 710 is configured to connect to a communications module 712. Exemplary communications modules 712 (e.g., communications modules 218 and 318) include networking interface cards, such as Ethernet cards and modems. In certain aspects, input/output module 710 is configured to connect to a plurality of devices, such as an input device 714 (e.g., main display 310) and/or an output device 716 (e.g., main display 310). Exemplary input devices 714 include a keyboard and a pointing device, e.g., a mouse or a trackball, by which a user can provide input to the computer system 700. Other kinds of input devices 714 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Exemplary output devices 716 include display devices, such as a LCD (liquid crystal display) monitor, for displaying information to the user.

According to one aspect of the present disclosure, PCU 100 and controller 110 can be implemented using a computer system 700 in response to processor 702 executing one or more sequences of one or more instructions contained in memory 704. Such instructions may be read into memory 704 from another machine-readable medium, such as data storage device 706. Execution of the sequences of instructions contained in main memory 704 causes processor 702 to perform the process steps described herein. One or more processors in a multi-processing arrangement may also be employed to execute the sequences of instructions contained in memory 704. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. The communication network can include, for example, any one or more of a LAN, a WAN, the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computer system 700 can include clients and servers. A client and server are generally remote from each other and typically interact through a communication network. The relationship of client and server arises by virtue of computer programs running on the respective computers and having a client-server relationship with each other. Computer system 700 can be, for example, and without limitation, a desktop computer, laptop computer, or tablet computer. Computer system 700 can also be embedded in another device, for example, and without limitation, a mobile telephone, a PDA, a mobile audio player, a Global Positioning System (GPS) receiver, a video game console, and/or a television set top box.

The term "machine-readable storage medium" or "computer readable medium" as used herein refers to any medium or media that participates in providing instructions to processor 702 for execution. Such a medium may take many forms, including, but not limited to, non-volatile media, volatile media, and transmission media. Non-volatile media include, for example, optical or magnetic disks, such as data storage device 706. Volatile media include dynamic memory, such as memory 704. Transmission media include coaxial cables, copper wire, and fiber optics, including the wires that include bus 708. Common forms of machine-readable media include, for example, floppy disk, flexible disk, hard disk, magnetic tape, any other magnetic medium, CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter affecting a machine-readable propagated signal, or a combination of one or more of them.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (e.g., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A computer-implemented method, comprising:
receiving, in a main frame of a patient care unit, a first indication that a first medication delivery module was electronically coupled to the main frame via a first plug-in port of the main frame; displaying, on a display of the main frame responsive to receiving the first indication, a first graphical channel card representative of the first medication delivery module and having a first visual indicator along an edge of the first graphical channel card, wherein the first visual indicator is configured to display information associated with a status of the first medication delivery module; dynamically orienting, responsive to receiving the first indication, the edge of the first graphical channel card and the first visual indicator in a direction toward the first plug-in port coupling the main frame to the first medication delivery module; receiving infusion information from the first medication delivery module via the first plug-in port; displaying, on the display of the main frame, within the first graphical channel card, at least a portion of the received infusion information; receiving a user selection at the main frame; and expanding the first graphical channel card to display a detailed portion of the infusion information upon receipt of a user selection.

2. The computer-implemented method of claim 1, wherein displaying the first graphical channel card on the display of the main frame comprises mirroring a display of the at least the portion of the infusion information at the first medication delivery module.

3. The computer-implemented method of claim 2, wherein display information is provided from the main frame to a display of the first medication delivery module to facilitate the display at the first medication delivery module.

4. The computer-implemented method of claim 1, wherein the first visual indicator comprises a graphical strip along the edge of the first graphical channel card, and displaying information associated with the status comprises displaying an indication of a fluid flow in the first visual indicator of the first graphical channel card when the first medication delivery module is delivering an infusion.

5. The computer-implemented method of claim 1, further comprising:
receiving a second indication that the first medication delivery module was electronically decoupled from the first plug-in port and then electronically coupled to the main frame via a second plug-in port of the main frame on a side of the main frame opposite the first plug-in port; and
dynamically reorienting, responsive to receiving the second indication, the edge of the first graphical channel card and the first visual indicator toward the second plug-in port.

6. The computer-implemented method of claim 1, further comprising:
receiving a second indication that a second medication delivery module was electronically coupled to the main frame via a second plug-in port of the main frame at a side of the main frame opposite the first plug-in port and the first medication delivery module; and
dynamically displaying, with the first graphical channel card, on the display of the main frame in response to receiving the second indication, a second graphical channel card oriented toward the second plug-in port and such that an edge of the second graphical channel card is oriented in a direction opposite the edge of the first graphical channel card.

7. The computer-implemented method of claim 1, wherein the first visual indicator comprises a color banner on a side of the first graphical channel card, a color of the color banner being dynamically selected based on the status of the first medication delivery module.

8. The computer-implemented method of claim 1, wherein expanding the first graphical channel card to display a detailed portion of the infusion information comprises adjusting a font size for the first graphical channel card to enhance a viewer perspective.

9. The computer-implemented method of claim 1, further comprising:
verifying, by the main frame, that the first medication delivery module is associated with a patient registered with the patient care unit.

10. The computer-implemented method of claim 1, wherein the main frame comprises a communications module, the computer-implemented method further comprising transmitting to a controller, via the communications module, the infusion information.

11. A system, comprising: a memory storing instructions; and one or more processors coupled with the memory and configured to execute the instructions to cause the system to: receive, in a main frame of a patient care unit, an indication that a first medication delivery module was electronically coupled with the main frame via a first plug-in port of the main frame; provide for display on a display device of the main frame, responsive to receiving the indication, a first graphical channel card representative of the first medication delivery module and having a first visual indicator along an edge of the first graphical channel card, wherein the first visual indicator is configured to display information associated with a status of the first medication delivery module; dynamically orient, responsive to receiving the indication, the edge of the first graphical channel card and the first visual indicator in a direction toward a location of the first plug-in port relative to the main frame; receive first infusion information from the first medication delivery module via the first plug-in port; provide for display on the display of the main frame, within the first graphical channel card, at least a portion of the received first infusion information; determine, after orientating the edge of the first graphical channel card, that a second medication delivery module was electronically coupled to the main frame via a second plug-in port of the main frame on a side of the main frame opposite to the first plug-in port; receive a second infusion information from the second medication delivery module; and dynamically provide a second graphical channel card for display on the display device of the main frame, adjacent to the first graphical channel card, with a second visual indicator along an edge of the second graphical channel card oriented toward the second plug-in port and oriented in a direction opposite the edge of the first graphical channel card.

12. The system of claim 11, wherein the main frame comprises a memory circuit, and the one or more processors are further configured to execute the instructions to store the first infusion information in the memory circuit.

13. The system of claim 11, wherein the one or more processors are further configured to receive a user selection of the first graphical channel card, and to execute the instructions to dynamically expand the first graphical channel card, from a first summary state to a second detail state, to display a detailed portion of the first infusion information upon receipt of the user selection, and to expand or contract the first graphical channel card based on a number of active channels in the patient care unit.

14. The system of claim 11, wherein the one or more processors are configured to execute the instructions to provide display information to a display of the first medication delivery module to facilitate the display at the first medication delivery module.

15. The system of claim 11, wherein the one or more processors further execute instructions to verify that the first medication delivery module is associated with a patient registered with the patient care unit.

16. The system of claim 11, wherein the main frame comprises a communications module configured to communicate with a controller remote from the main frame over an electronic network, and the one or more processors further execute instructions to transmit to the controller, via the communications module, the first infusion information.

17. A non-transitory, computer-readable medium storing instructions which, when executed by a processor in a computer, cause the computer to perform a method, the method comprising: receiving, in a main frame of a patient care unit, a first indication that a first medication delivery module was electronically coupled with the main frame via a first plug-in port of the main frame; displaying, on a display of the main frame responsive to receiving the first indication, a first graphical channel card representative of the first medication delivery module and having a first visual indicator along an edge of the first graphical channel card, wherein the first visual indicator is configured to display information associated with a status of the first medication delivery module; dynamically orienting, responsive to receiving the first indication, the edge of the first graphical channel card and the first visual indicator in a direction toward a location of the first plug-in port of the main frame; receiving infusion information from the first medication delivery module via the first plug-in port; displaying, on the display of the main frame, within the first graphical channel card, at least a portion of the received infusion information; and expanding the first graphical channel card, from a first summary state to a second detail state, to display a detailed portion of the infusion information upon receipt of a user selection.

18. The non-transitory, computer readable medium of claim 17, wherein in the method, displaying the first graphical channel card in the main frame comprises mirroring a display in the first medication delivery module.

19. The non-transitory, computer readable medium of claim 17, the method further comprising:
receiving a second indication that the first medication delivery module was electronically decoupled from the first plug-in port and then electronically coupled to the main frame via a second plug-in port associated with the main frame on a side of the main frame opposite the first plug-in port; and
dynamically reorienting the edge of the first graphical channel card and the first visual indicator toward the second plug-in port.

20. The non-transitory, computer readable medium of claim 17, the method further comprising:
receiving a second indication that a second medication delivery module was electronically coupled to the main frame via a second plug-in port of the main frame at a side of the main frame opposite the first plug-in port and the first medication delivery module; and
dynamically displaying, with the first graphical channel card, on the display of the main frame in response to receiving the second indication, a second graphical channel card oriented in a direction toward the second plug-in port and such that an edge of the second graphical channel card is oriented in a direction opposite the edge of the first graphical channel card, the second graphical channel card including at least a portion of a second infusion information.

* * * * *